(12) United States Patent
Furukawa

(10) Patent No.: US 7,938,811 B2
(45) Date of Patent: May 10, 2011

(54) ATHLETE'S FOOT TREATMENT TOOL

(76) Inventor: Takashi Furukawa, Nagoya (JP)

( * ) Notice: Subject to any disclaimer, the term of this patent is extended or adjusted under 35 U.S.C. 154(b) by 0 days.

(21) Appl. No.: 11/878,229

(22) Filed: Jul. 23, 2007

(65) Prior Publication Data
US 2008/0015525 A1    Jan. 17, 2008

Related U.S. Application Data

(63) Continuation-in-part of application No. 10/759,292, filed on Jan. 16, 2004, now abandoned.

(30) Foreign Application Priority Data

| Jan. 22, 2003 | (JP) | 2003-050080 |
| Feb. 2, 2003 | (JP) | 2003-062498 |
| Jun. 16, 2003 | (JP) | 2003-199487 |

(51) Int. Cl.
*A61M 35/00* (2006.01)

(52) U.S. Cl. ........ 604/293; 604/289; 604/290; 604/292; 2/158; 2/159; 2/164; 2/169

(58) Field of Classification Search .................. 604/290, 604/293
See application file for complete search history.

(56) References Cited

U.S. PATENT DOCUMENTS

| 3,882,868 | A | * | 5/1975 | Tundermann | 604/293 |
| 4,341,096 | A | * | 7/1982 | Safrit et al. | 66/185 |
| 4,589,994 | A | * | 5/1986 | Moseman | 424/770 |
| 4,622,035 | A | * | 11/1986 | Palmer et al. | 604/293 |
| 4,820,279 | A | * | 4/1989 | Dedo | 604/290 |
| 5,682,617 | A | * | 11/1997 | Tumas | 2/239 |
| 5,867,839 | A | * | 2/1999 | Lawlor | 2/240 |
| 6,896,667 | B2 | * | 5/2005 | Carter | 604/292 |
| 2003/0223982 | A1 | * | 12/2003 | Schlotmann et al. | 424/94.61 |

FOREIGN PATENT DOCUMENTS

| JP | U-59-36346 | 3/1984 |
| JP | U-59-177446 | 11/1984 |
| JP | U-61-203014 | 12/1986 |
| JP | A-1-125326 | 5/1989 |
| JP | U-1-172849 | 12/1989 |
| JP | A-2-56436 | 2/1990 |
| JP | A-2-98370 | 4/1990 |
| JP | A-5-76404 | 3/1993 |
| JP | A-9-21001 | 1/1997 |
| JP | A-11-178850 | 7/1999 |

(Continued)

*Primary Examiner* — Tatyana Zalukaeva
*Assistant Examiner* — Ilya Y Treyger
(74) *Attorney, Agent, or Firm* — Oliff & Berridge, PLC

(57) ABSTRACT

With the effect of alcohol, components of athlete's foot medicine penetrate deeply into the skin and athlete's foot is cured early and completely. The athlete's foot treatment liquid is a mixture of athlete's foot medicine and alcohol, which has a feature of penetrating into the skin well. The athlete's foot treatment liquid permeates well into the inner sock. It permeates all over the sock by capillarity. The impermeable bag, which does not have liquid medicine leak out, is worn on the inner sock. The impermeable bag is filled with the athlete's foot treatment liquid. The opening of the impermeable bag is closed tightly with the rubber band so as not to have the athlete's foot treatment liquid permeate, evaporate or leak out. The outer sock is worn on the impermeable bag. The impermeable bag is compressed inward, so that the athlete's foot treatment liquid is pushed up to an upping line.

20 Claims, 2 Drawing Sheets

FOREIGN PATENT DOCUMENTS

| | | |
|---|---|---|
| JP | 2002363070 A * | 12/2002 |
| JP | A-2003-231630 | 8/2003 |
| JP | A-2003-235989 | 8/2003 |
| JP | A-2004-91458 | 3/2004 |
| JP | A-2004-224787 | 8/2004 |
| JP | A-2004-231631 | 8/2004 |
| JP | A-2005-7103 | 1/2005 |
| JP | A-2006-36742 | 2/2006 |
| JP | A-2006-56865 | 3/2006 |
| JP | A-2007-99753 | 4/2007 |

* cited by examiner

ATHLETE'S FOOT TREATMENT TOOL

This is a Continuation-in-Part of application Ser. No. 10/759,292 filed Jan. 16, 2004, now abandoned and claims the benefit of Japanese Application Nos. 2003-050080 filed Jan. 22, 2003, 2003-062498, filed Feb. 2, 2003 and 2003-199487, filed Jun. 16, 2003. The disclosure of the prior applications is hereby incorporated by reference herein in its entirety.

BACKGROUND

1. Field of the Invention

The present invention relates to an athlete's foot treatment tool (utensil).

2. Description of Related Art

In conventional remedies for athlete's foot, a sunlamp is irradiated or a small dose of medicine is applied to the affected part. But a sunlamp is not able to reach all over the affected part thoroughly as digits make shadow of the sunlamp.

Alcoholic or a spray-on type of medicine gets dry too quickly to cure athlete's foot completely. Oil-based medicine does not penetrate into the skin deeply enough to eradicate athlete foot bacillus. Athlete's foot bacillus generally stays in a horny layer but often penetrates deeply into the derma though the epidermis. That's because it has been difficult to cure athlete's foot completely. Even if athlete's foot seems to be cured, it often recurs.

The published patent applications relating to the present invention are as follows:
(1) Japanese patent publication No. 9-21001
(2) Japanese patent publication No. 2003-235989
(3) Japanese patent publication No. 2004-231631
(4) Japanese patent publication No. 2004-224787
(5) Japanese patent publication No. 2004-91458
(6) Japanese patent publication No. 2003-231630
(7) Japanese patent publication No. 2005-7103

SUMMARY

One of the conventional remedies for athlete's foot provides a treatment which applies extracts of athlete's foot medicine or althea to the affected part. But the applied extracts of the athlete's foot medicine or althea do not penetrate deeply into the derma and get dry too quickly to take effect.

The present invention is to solve the above problems. An object of the present invention is to kill bacillus widely and thoroughly which has deeply penetrated into the derma through the epidermis so that athlete's foot can be completely extinguished never to recur.

In order to achieve the said object, the present invention implements athlete's foot treatment liquid which is a mixture of athlete's foot medicine or liquid components extracted from althea and alcohol: an inner sock permeated with the athlete's foot treatment liquid to wear on a foot: an impermeable bag which is filled with the said treatment liquid and is closed around the ankle not to let the medicine permeate through, evaporate or leak out: an outer sock to wear on the impermeable bag and compress the bag from outside.

(1) Effect of the Structure

The impermeable bag does not allow the athlete's foot treatment liquid to permeate through, evaporate or leak out. The bag is closed around the ankle. Accordingly alcohol does not evaporate, the athlete's foot treatment liquid does not get dried, and components of the athlete's foot medicine or althea penetrate deeply into the skin, so that athlete's foot can be eradicated early. As the whole foot or hand is covered with the impermeable bag containing the athlete's foot treatment liquid, any part of the foot or the hand in contact with athlete's foot bacillus can be covered with the liquid.

In addition the outer sock or glove compresses the impermeable bag inward and the said athlete's foot treatment liquid in the impermeable bag is pushed up. As a result a small amount of the athlete's foot treatment liquid is enough to spread all over the foot or the hand and to take effect widely on the foot or the hand for a long time.

(2) Effect of Mixing Athlete's Foot Medicine or Extracted Components of Althea and Alcohol Alcohol helps extracted components of athlete's foot medicine or althea keep penetrating from the surface of a foot or a hand. It means that treatment for athlete's foot continues while the components keep penetrating. If the athlete's foot treatment liquid got dried during the treatment, the athlete's foot medicine or extracted components of althea could not take good effect.

In order to make the treatment effective, alcohol should be contained more than or several times as much as the athlete's foot medicine or extracted components of althea. Otherwise particles/molecules of the athlete's foot medicine or extracted components of althea cannot be wrapped by particles/molecules of alcohol or cannot be dissolved well, and the athlete's foot medicine or extracted components of althea cannot be penetrated and absorbed effectively into the hand or the foot soaked in the athlete's foot treatment liquid in the impermeable bag.

The way of making the above athlete's foot treatment liquid is to first put athlete's foot medicine or althea into water, whose volume, cubic content and weight are larger, preferably several times, more preferably 1 to 12 times or more preferably 2 times as large as those of the athlete's foot medicine or althea. Then they are boiled and decocted into liquid extract of the athlete's foot medicine or althea. The liquid extract of the athlete's foot medicine or althea is mixed with alcohol whose volume, cubic content and weight are larger than, preferably several times, more preferably 0.1 to 99.9 times, more preferably 5 to 15 times or more preferably 10 times as large as those of the liquid extract.

Then particles/molecules of the athlete's foot medicine or extracted components of althea are wrapped by particles/molecules of alcohol, and the athlete's foot medicine or the extracted components of althea are dissolved in alcohol well. Consequently the components of athlete's foot medicine or althea can be penetrated and absorbed effectively into the horny layer, the epidermis and the derma of the foot or the hand. As there is not much room in the impermeable bag covering the foot or the hand, the athlete's foot treatment liquid cannot be penetrated and absorbed into the foot or the hand effectively unless the athlete's foot medicine or the extracted components of althea are mixed with alcohol at the best ratio.

If the foot or the hand moves in the impermeable bag, the skin of the foot or the hand moves and the athlete's foot treatment liquid, in which the athlete's foot medicine or the extracted components of althea are mixed with alcohol, is stirred well. As a result the athlete's foot medicine or the extracted components of althea are not separated from alcohol. They are stirred well and are penetrated and absorbed effectively into the foot or the hand. If the athlete's foot medicine or the extracted components of althea were separated from alcohol, the best ratio of mixing the athlete's foot medicine or the extracted components of althea and alcohol would not be kept partly.

As the athlete's foot treatment liquid, which is a mixture of the athlete's foot medicine or the extracted components of althea and alcohol, is contained hermetically in the impermeable bag, the alcohol does not evaporate and the best ratio of mixing the athlete's foot medicine or the extracted components of althea can be kept. Therefore the athlete's foot medicine or extracted components of althea are penetrated and absorbed into the foot or the hand effectively.

Figure 1:
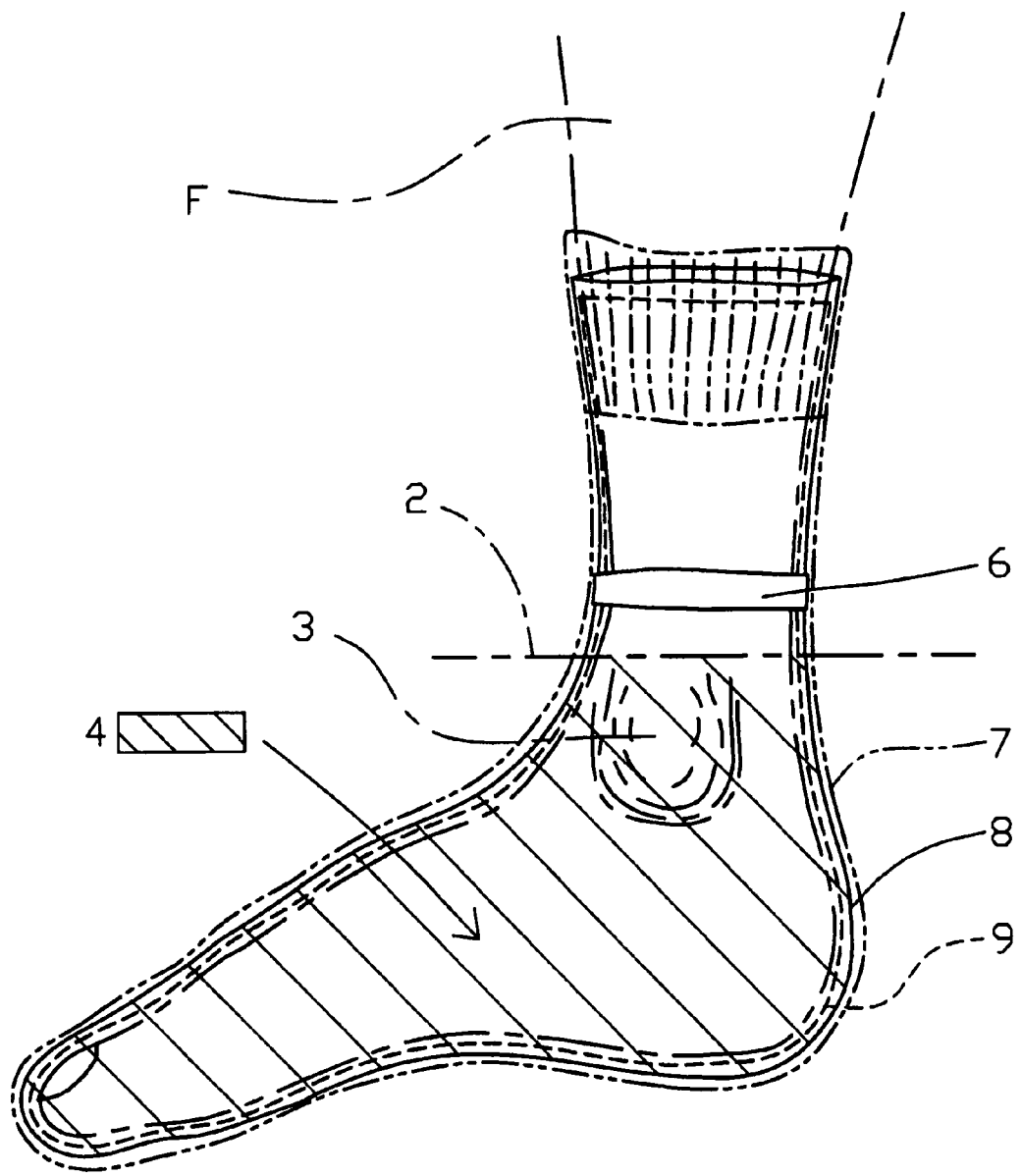
FIG. 1 is a section illustrating the athlete's foot tool (utensil) of the present invention worn on a foot.

DETAILED DESCRIPTION OF EMBODIMENTS (1) Athlete's Foot Treatment Liquid 4

The athlete's foot treatment liquid 4 is a mixture of the athlete's foot medicine or extracted components of althea, or the liquid of the extracted components, and alcohol. Althea is a deciduous shrub belonging to a hollyhock family. Barks of the trunks, stems, branches and roots are mainly used to make the athlete's foot treatment liquid 4. The leaves, flowers and buds can be used as well as a core of the trunks, stems, branches and roots.

Scores of grams, for example, 20 grams/20 weight of small pieces, grains or powder of althea's dried bark are added to some hundred cc of water, for example, 200 cc/200 volume. Then it is boiled and decocted at 80 to 100° for one to several hours for example 2 hours, or for several minutes to some scores of minutes for example 30 to 60 minutes to make scores of grams for example 4 grams/4 weight/40 cc/4 volume of liquid extract of althea. The liquid contains much or condensed extract of althea.

The athlete's foot medicine sold commercially is used. It is aqueous, oleaginous or belongs to alcohol, azole, imidazole, triazole, ally amine, N-hydroxypyridone, thiocarbamide, benzylamine, morpholine, hydrochloric acid, nitric acid or salicylic acid family. The major components are kerokozonarl hydrochloride, isoconazole nitrate, econazole nitrate, or amorolfin hydrochloride etc.

How to make the athlete's foot treatment liquid 4 is to mix the liquid extracts of the components of the athlete's foot medicine or althea with several hundred cc, for example, 250 to 260 cc/250 to 260 volume of liquid alcohol. The concentration of the liquid alcohol is 5 to 100% by volume, preferably 20 to 95% by volume, more preferably 40 to 90% by volume, or much more preferably 60 to 85% by volume, that is for example about 80% by volume. The liquid alcohol contains proper volume of water/refined water/pure water to achieve such concentration.

When the components of athlete's foot medicine or althea are extracted into water, they can be mixed with alcohol better and athlete's foot medicine or the extracted components of althea can penetrate into the skin better. When the athlete's foot medicine or the extracted components of althea are mixed with alcohol, they can penetrate into the skin more deeply. Athlete's foot medicine and components of althea are extracted and condensed, and they are effective as medicine.

The liquid extract of the components of althea may be made by soaking 20 g of small pieces, grains or powder of the bark of althea into several hundred cc, for example 250 to 400 cc, more specifically for example 300 cc of liquid alcohol directly. The time of soaking it in liquid alcohol directly is scores of hours to several days, scores of days or several months, and preferably one month to several months.

The liquid alcohol is ethyl alcohol ($C_2H_5OH$) or ethanol, which may be either drinking or rubbing alcohol. Alcoholic drinks that do not have strong taste or color are also applicable such as shochu (Japanese clear liquor) and vodka. They are penetrated and absorbed well into the skin. Shochu contains 20 to 50% by volume, for example, 35% by volume of alcohol. Vodka contains 40 to 60% by volume, for example, 50% by volume of alcohol.

Another way to extract components of althea is to soak the small pieces, grains or powder of the bark of althea into several hundred cc, for example, 250 to 260 cc of liquid salicylic acid, liquid glycerin or other solvents which are easily penetrated and absorbed into the skin. The time to soak it directly in liquid salicylic acid is scores of hours to several days, or scores of days to several months.

As stated above, how to make the athlete's foot treatment liquid is to boil athlete's foot medicine or althea in water and decoct them to get liquid extract. The volume of water should be larger than, preferably several times, more preferably 1 to 12 times or more preferably 2 times as large as that of the athlete's foot medicine or althea. Then the liquid extract is mixed with alcohol. The volume of alcohol should be larger than, preferably several times, more preferably 0.1 to 99.9 times, more preferably 5 to 15 times or more preferably 10 times as large as that of the liquid extract of the athlete's foot medicine or althea.

In this athlete's foot treatment liquid, particles/molecules of the components of athlete's foot medicine or extracts of althea are wrapped by particles/molecules of alcohol and it allows the components to be penetrated and absorbed into a foot or a hand most effectively. As there is not much room in the impermeable bag covering the foot or the hand, the athlete's foot treatment liquid cannot be penetrated or absorbed into the foot or the hand effectively unless the athlete's foot medicine or extracted components of althea are mixed with alcohol at the best ratio.

The said liquid extract may be frozen at 0° C., −5° C., −10° C. or below the temperatures. The frozen extract may be dried and powdered. In the frozen, dried or powdered state, the athlete's foot medicine or extracted components of althea can be preserved for a long period of time, which makes mass production of the athlete's foot treatment liquid 4 easier. Such frozen and dried powder of the athlete's foot medicine or extracted components of althea is convenient to carry. A patient can supply the athlete's foot tool (utensil) with the athlete's foot treatment liquid 4 by dissolving the powder in alcohol while he is away from home.

Such freeze-dried powder of the athlete's foot medicine or extracted components of althea is made into the said athlete's foot treatment liquid 4 by being dissolved in the said alcohol. Water may be added. Freeze-dried powder of the athlete's foot medicine or extracted components of althea can be dissolved more easily in the said alcohol. Therefore they can be penetrated and absorbed into the skin more effectively. As a result the athlete's foot treatment liquid 4 takes more curative effect with a smaller amount of the extract dissolved in it.

(2) Method of Making Freeze-Dried Powder of The Athlete's Foot Medicine Extracted Components of or Althea In order to make freeze-dried powder of the athlete's foot medicine or extracted components of althea, it is necessary to refrigerate and freeze quickly the solution of the said extracts of athlete's foot medicine or althea. Then the freeze-dried extracts are put into the airtight container, in which the air pressure is lowered or a vacuum is formed. In such an atmosphere the boiling point of water is lower and it is only water that gets sublimed and evaporates, so that the extracts get dried to become powder/granule. In this way the athlete's foot medicine or extracted components of althea are powdered.

The said liquid extracts of the components of athlete's foot medicine or althea, which have been quickly refrigerated/frozen, may be dehydrated/vaporized to dry. The dried extracts are ground into powder/granule. This is another way of make the freeze-dried extracts.

(3) Athlete's Foot Tool (Utensil) for the Foot F

FIG. 1. illustrates the section of the athlete's foot tool (utensil) for the foot F. First the inner sock 9 is worn on the foot F. The inner sock 9 is a woven textile sock sold on the market. It is elastic and very thin so as to allow the said athlete's foot treatment liquid 4 to penetrate by capillarity. The inner sock 9 has a separated toe to cover each digit like a cap, but the toe does not necessarily have to be separated, the inner sock 9 may be mesh-type, puttees-type, band-type etc.

The impermeable bag 8 is worn on the inner sock 9. The impermeable bag 8 is made of synthetic resins such as polyethylene, polypropylene, polyester, vinyl, etc. It is watertight and it does not let the said athlete's foot treatment liquid 4 permeate through, leak out or evaporate.

The impermeable bag 8 has no holes and is sealed up. The bag is filled with 10 to 100 cc/g or preferably 30 to 50 cc/g of the athlete's foot treatment liquid 4 made in the above-mentioned way. It does not let the athlete's foot treatment liquid 4 leak out or evaporate. The ring-shaped rubber band 6 closes tightly the opening of the impermeable bag 8 around the ankle, so that the impermeable bag 8 is sealed up hermetically not to let the athlete's foot treatment liquid leak out or evaporate, and in addition the opening of the impermeable bag 8 does not get slipped down.

The rubber band 6 closes the opening of the impermeable bag 8 tightly to seal it up. So even if a patient walks or moves his leg, the athlete's foot treatment liquid does not leak out of the bag.

Inside the impermeable bag 8 the athlete's foot treatment liquid 4 permeates into the inner sock 9 to the extent that no drops or only a few drops drip from the inner sock 9. Therefore if a patient lifts up his leg or gets the bag upside down, the athlete's foot treatment liquid 4 does not leak out. The athlete's foot treatment liquid 4 may be contained as much as lots of drops drip from the inner sock 9. FIG. 1 illustrates that the athlete's foot treatment liquid 4 is filled to an upping line 2, but actually the athlete's foot treatment liquid 4 penetrates to the lower edge of the rubber band 6 by capillarity.

The impermeable bag 8 is a square. It may also be a foot-shaped bag, a rubber tabi: a sock cloven at the big toe, a rubber sock, a bag cloven at each toe, or a plastic bag of a supermarket. However, if the impermeable bag 8 is too big or too thick to fit a foot, extra amount of the athlete's foot treatment liquid 4 is needed.

Instead of the said rubber band 6, the opening of the said impermeable bag may be bound with a string, tape, belt, fastener or hook-and-loop fastener. The said supermarket's bag may also be applicable with the handles tightened around the ankle. A string or something else to tighten the bag may be integrated around the opening of the impermeable bag 8. Or the opening of the impermeable bag 8 may be folded outside to provide a rim to include the rubber band 6 inside.

In such ways the impermeable bag 8 is sealed hermetically and the athlete's foot treatment liquid 4 does not leak out or evaporates. The rubber band 6 may not always be outside of the impermeable bag 8 but outside of the outer sock 7 as described later.

The outer sock 7 is worn outside of the said impermeable bag 8. A commonly sold sock is suitable for the outer sock 7, which should be an elastic woven textile. The toe may be separated to cover each digit like a cap. The outer sock 7 may be mesh-type, puttees-type, band-type etc.

The outer sock 7 is elastic, and so it tightens inward the impermeable bag 8 filled with the athlete's foot treatment liquid 4. As a result the said athlete's foot treatment liquid 4 is pushed up and reaches the upping line 2 above the ankle 3. Therefore a small amount of the athlete's foot treatment liquid 4 is enough to spread effectively all over the surface of the foot, and the effect continues widely for a long time.

There is a room between the above-mentioned impermeable bag 8, the inner sock 9 and the foot and the inner sock 9 has capillarity. The room allows the athlete's foot treatment liquid 4 to permeate smoothly into the whole inner sock 9. And also the room prevents the impermeable bag 8 from getting damaged or broken if a patient walks or moves his leg with the athlete's foot tool (utensil) on. The above-mentioned outer sock 7 compresses the bag inward, so that the above-mentioned room is compressed and becomes smaller and the athlete's foot treatment liquid 4 is pushed up as mentioned above.

The opening of the said inner sock 9 is lower and nearer to the toe than the tightening position of the rubber band 6 of the said impermeable bag 8. Therefore the athlete's foot treatment liquid 4 does not leak out of the impermeable bag 8 through the inner sock 9.

The tightening position of the rubber band 6 or the opening of the said impermeable bag 8 is lower and nearer to the toe than the said outer sock 7. As a result the tightening position of the rubber band 6 or the opening of the impermeable bag 8 is covered with the outer sock 7. The tightening position of the rubber band 6 or the opening of the impermeable bag 8 may be out of the outer sock 7.

(4) Athlete's Foot Tool (Utensil) for a Hand (H)

Figure 2:
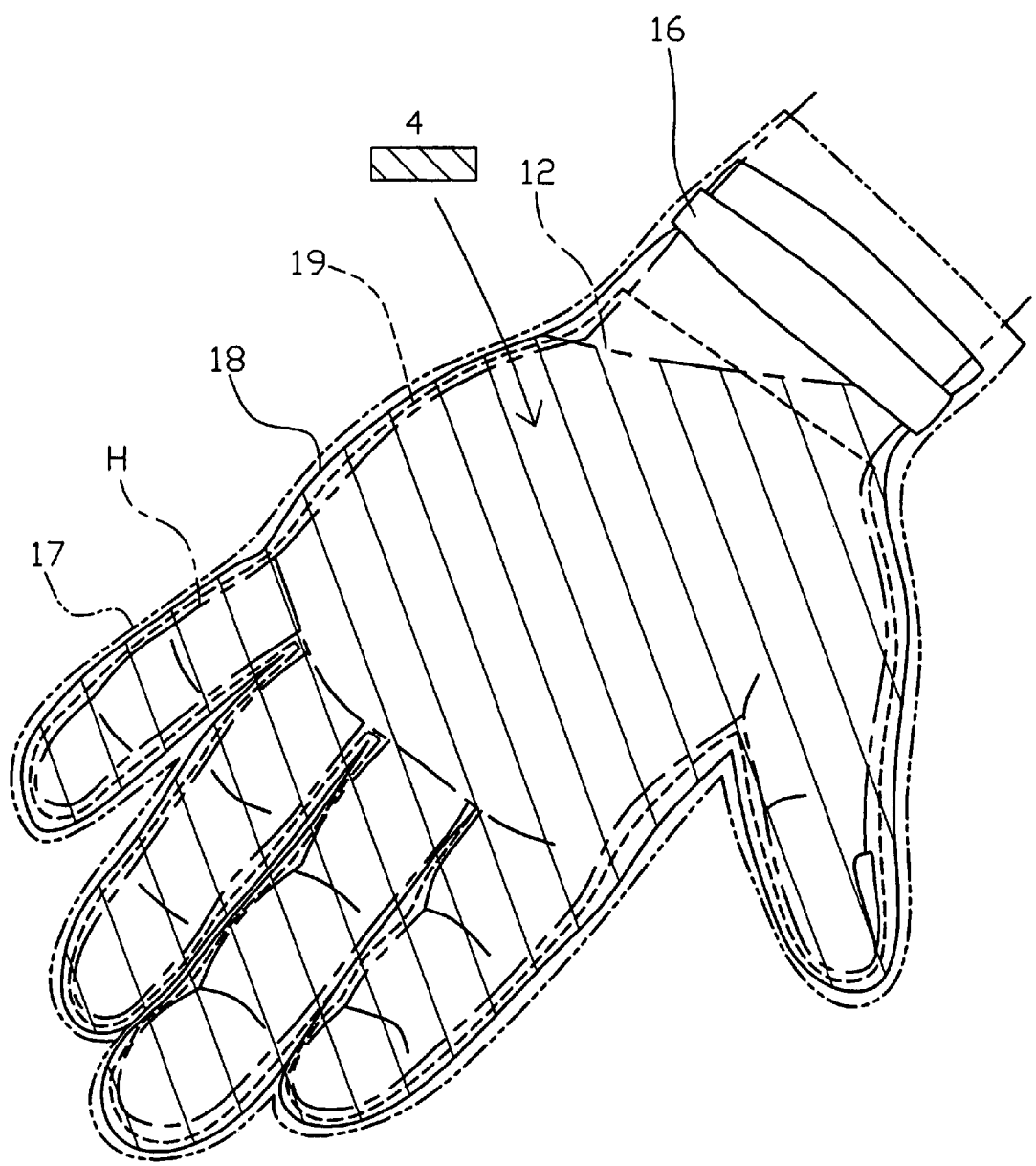
FIG. 2 is a section illustrating the athlete's foot tool (utensil) of the present invention worn on a hand.

FIG. 2 illustrates a section of the athlete's foot tool (utensil) for a hand H. The inner glove 19 is worn on the hand H. The impermeable bag 18, which does not let the athlete's foot treatment liquid through, is worn on the inner glove 19. The outer glove 17 is worn on the impermeable bag 18.

The structures, shapes, materials of the inner glove 19, the impermeable bag 18 and the outer glove 17 are the same as those of the inner sock 9, the impermeable bag 8 and the outer sock 7. However, the shapes are made suitable for a hand not for a foot.

The inner bag 19 is smaller than the impermeable bag 18 and the opening of the inner glove 19 is nearer to the fingertips than is the tightening position of the rubber band 16 of the impermeable bag 18. Therefore the athlete's foot treatment liquid 4 does not leak out of the impermeable bag 18 through the inner glove 19.

The impermeable bag 18 is smaller than the outer glove 17 and the tightening position of the rubber band 16 or the opening of the impermeable bag 18 is nearer to the fingertips than is the opening of the outer glove 17. Therefore the tightening position of the rubber band 16 or the opening of the impermeable bag 18 is covered with the outer glove 17. The said tightening position of the rubber band 16 or the opening of the impermeable bag 18 may be out of the outer glove 17.

(5) How to Use the Athlete's Foot Tool (Utensil)

(a) Wear the athlete's foot tool (utensil). Soak a foot or a hand in the athlete's foot treatment liquid 4 for scores of minutes to 1 hour once or more than once a day. Then the athlete's foot treatment liquid 4 will penetrate into the epidermis.

(b) Two pairs of shoes are necessary. Pour 20 to 50 cc of alcohol which has a strong sterilizing power into each shoe. Stir the alcohol with a cotton-wound stick so as to have the alcohol penetrate into the whole shoe. Then dry the shoes naturally. Or spray alcohol twice or three times to the inside of each shoe.

(c) Keep the inner sock 9, the inner glove 19, the outer sock 7 and the outer glove 17 sterilized and disinfected in boiling water or a disinfectant before use.

(d) Keep soaking the foot or the hand every day as mentioned above. Then the epidermis becomes scaly and peeled off. Continue soaking every day as mentioned above until the epidermis gets peeled off three times. When the foot or the hand looks cleared, the remedy is over.

(e) The inner sock 9 or the inner glove 19 is sterilized and disinfected. The athlete's foot treatment liquid 4 in the impermeable bags 8, 18 is used repeatedly. The athlete's foot treatment liquid 4 is supplemented each time it becomes less.

(f) Athlete's foot bacillus exists anywhere. It is very infectious. If it infects once, it tends to infect repeatedly. In this method athlete's foot is treated several times a year. Two pairs of sterilized and disinfected shoes are exchanged to wear every week, or shoes are sterilized with alcohol every week. Then athlete's foot bacillus and bacteria do no not propagate any more and bad smell of shoes vanishes off.

(g) A bathroom's floor or a mat is infected additionally.

(h) Necessary cares must be taken as alcohol has to be used in this treatment. Alcohol penetrates and is absorbed from a hand or a foot into a body. When a patient drives a car, the athlete's foot tool (utensil) must not be used.

(i) Athlete's foot medicine or althea is not harmful if they penetrate or are absorbed into a human's body. When they are orally taken, they take various effects as medicine. When a part or all of their components dissolved in alcohol penetrate or are absorbed through a hand or a foot they take other various effects than cure athlete's foot and they are not harmful to a human's body.

(6) The Second Embodiment

The curative medicine and tools for the athlete's foot with medicine liquid and high concentration alcohol.

This invention uses the athlete's foot medicine and high concentration alcohol of the conventional marketing, and relates to the tools and the medical treatment method and using the prepared thing and its simple substance. There is nothing that can carry out perfect recovering of the athlete's foot, although the medicine manufacture companies in the world have made much athlete's foot medicine from the former. The present condition is that the man in the world moreover also desires extermination and perfect recovering for athlete's foot for a short period of time now.

It relates to finding the way that the man in the world was in trouble for years and full medical treatment was studied. It acts with a little athlete's foot medicine in high concentration alcohol, the leg was immersed per time, and it invented perfect recovering for the athlete's foot bacillus for a short period of time.

This invention is explained in detail. An athlete's foot has the concept what is not cured and everybody has an idea near abandonment. Even when it seemed that medicine is applied and it healed up, I thought that it came out again. This invention tried to act as perfect recovering of the athlete's foot for a short period of time. The medical treatment method is described below.

(A) The retail medicine from the manufacture companies—10~20 Vol. % to rubbing alcohol into the rubbing alcohol of—79 Vol. %—makes the athlete's foot curative medicine liquid diluted to 5 to 10 times from the high concentration alcohol which makes order the optimal.

(B) Prepare the bag with which the liquid will not carried out during the legs being immersed.

(C) Put legs into D, and wear, binding bags and extracting socks or the bags of elasticity on it.

(F) Thin socks may be worn into a bag.

(G) Each of the A-B-C are put into the bag, and put over than ankle or even than the medical treatment range, and the skin of legs will become like fish scales, and continue about one week twice in the morning and in evening for one day, and it separates being immersed for several minutes to 1 hour or more, it will be stopped. It finishes when they separate. And at the time of a serious illness, and it will need to repeat the same way again.

(H) Disinfect inside of the shoes every day with the rubbing alcohol.

(I) Disinfected socks must be used each time. It is for preventing re-infection on foot.

(J) Also disinfected and sterilize the mat in the bathroom—and others in the same way are needed. The above medical treatment methods are for extinguishing athlete's foot bacillus from the feet and life circumference so that a curative medicine's may be made to permeate to the dermis to which an athlete's foot bacillus breeds, an athlete's foot bacillus's may be killed and it may not recur.

This is explanation for wearing bags and socks on feet which are familiarized with legs, and puts either of the A-B-C in into a bag.

(a) Foot
(b) Waterproof bag
(c) Socks which keep the liquid
(d) Binding up the Bag
(e) Putting the liquid to the bag
(f) The line which indicates the liquid comes up Old Claim (A) The retail medicine from the manufacture companies which melts into the rubbing alcohol of −79 VOl %—makes the athlete's foot curative medicine liquid diluted 5 to 10 times from the high concentration alcohol which makes order the optimal.

(B) Preparing the required quantity of the following medical treatment method for the athlete's foot medicine of each medicine manufacture companies.

(C) Preparing the high concentration rubbing alcohol 79 VOl %—which makes order the optimal (D) Preparing the bags liquid leak of the leg is not carried out for being immersed.

(E) Binding up the bags in which the legs immersed. Preparing socks or the bags of elasticity.

(F) Putting each of the A-B-C into the bag, and steeping over than ankles or over than the medical treatment range till the skin of legs will become like fish scales, and continue about one week twice in the morning and in evening for one day till it separates being immersed for several minutes to 1 hour or more, then being stopped. And finish when they separate. And at the time of a serious illness, it will be needed repeating the same thing again.

The athlete's foot had a concept of that which cannot be healed up very easily. It is because that the medical treatment method is not suitable. I have invented the immersing medical treatment method by the time unit with the retail medicine from the manufacture companies and rubbing alcohol to permeate into dermis.

(7) Description of the Other Embodiments

The present invention is not limited to the said embodiment, but is able to be applied in various ways. For example, small pieces, grains or powder of the said athlete's foot medicine or dried althea's bark may be put into the impermeable bags 8, 18 with alcohol. Then the inner sock 9, the impermeable bag 8, 18 and the outer sock 7, or the inner glove 19, the impermeable bag 8, 18 the outer glove 17 may be worn. Also in this way the athlete's foot medicine or extracted components of the althea keep penetrating into the foot or the hand. As they are not dried halfway, the effects do not disappear and continue.

There may or may not be a room between the foot and the inner sock 9 or between the hand and the inner glove 19. There may or may not be a room between the foot, the inner sock 9 and the impermeable bag 8 or between the hand, the inner glove 19 and the impermeable bag 18. There may or may not be a room between the foot, the inner sock 9, the impermeable bag 8 and the outer sock 7 or between the hand, the inner glove 19, the impermeable bag 18 and the outer glove 17.

When the room is small/none, a smaller amount of the athlete's foot treatment liquid 4 is enough to spread all over the surface of the foot or the hand by capillarity. When the room is larger, more athlete's foot treatment liquid 4 can be filled and it does not have to be added frequently. The athlete's foot treatment liquid 4 penetrates more into the foot or the hand.

The impermeable bags 8, 18 are larger than the inner sock 9 or the inner glove 19. The outer sock 7 or the outer glove 17 is larger than the impermeable bags 8, 18 and the inner sock 9 or the inner glove 19, which makes wearing them easier. However, the sizes may be reversed. In such a case the impermeable bags 8, 18, the inner sock 9 and the inner glove 19 are compressed from outside.

If the impermeable bags 8, 18 are as strong and compressive as rubber socks or rubber gloves, the outer sock 7 and the outer glove 17 do not have to be worn. If the impermeable bags 8, 18 are strong enough and larger than the foot or the hand, the inner sock 9 and the inner glove 19 do not have to be worn.

The said rubber bands 6, 16 are not always necessary. When they are not used, a patient has to try to keep his foot or hand unmoved. Only the impermeable bags 8, 18 may be put on with the athlete's foot treatment liquid in it. In this case the rubber bands 6, 16 have to be very compressive and the impermeable bags 8, 18 have to be very strong.

The said athlete's foot tool (utensil) is also able to be applied to lower legs, thighs, forearms, upper arms and other parts infected with athlete's foot bacillus. For such applications, the inner sock 9, the impermeable bags 8, 18, the inner glove 19, and in some cases the outer sock 7 and the outer glove 17 have to be longer than the ankle or the wrist. Or these outfits 9, 8, 18, 19, 7 and 17 are cylindrical and fastened at the both ends with the rubber band 6.

(8) The Other Effects of the Present Invention

Claims 1, 2: by virtue of the present invention, the athlete's foot medicine with alcohol penetrates deeply into the skin, and athlete's foot is cured completely. In the present invention, the impermeable bag prevents alcohol from evaporating and the athlete's foot treatment liquid from getting dried. As a result the athlete' foot medicine penetrates deeply into the skin and athlete's foot is completely cured early.

The athlete's foot treatment liquid in the impermeable bag is pushed up by the compression of the outer sock or the outer glove. Accordingly, a small amount of the athlete's foot treatment liquid is enough to spread all over the surface of a foot or a hand.

Claims 3, 4: alcohol helps the athlete's foot medicine or extracted components of the althea keep penetrating through the surface of the foot or the hand, and treatment for athlete's foot continues. The athlete's foot medicine or the extracted components of althea would not work effectively if they got dried. But it is not caused.

Claims 5, 6: by this mixing ratio, particles/molecules of the athlete's foot medicine are well wrapped by particles/molecules of alcohol, and the athlete's foot medicine or the extracted components of althea can be penetrated and absorbed effectively into the hand or the foot which is soaked in the athlete's foot treatment liquid in the impermeable bag.

Claim 7: the athlete's foot treatment liquid does not leak out even if the patient moves his leg or walks with the athlete's foot tool (utensil) on.

Claim 8: the athlete's foot treatment liquid does not leak out even if the patient moves or lifts his hand with the athlete's foot tool (utensil) on.

Claims 9, 10: the athlete's foot treatment liquid does not permeate through the inner sock or the inner glove out of the impermeable bag. The tightening position or the opening of the impermeable bag is covered with the outer sock or the outer glove.

The athlete's foot medicine described in claim 1, wherein the inner sock or the inner glove soaked into the athlete's foot treatment liquid contains as much liquid as only a few or no drops drip. As a result the athlete's foot treatment liquid does not leak out if a hand or a foot is moved to be upside down.

Claims 11, 12: the impermeable bag is not damaged or broken even if the patient walks, moves his leg, moves or lifts his hand with the athlete's foot tool (utensil) on.

Claims 13-16: the athlete's foot tool (utensil) described in claim 1, wherein the concentration of alcohol is 5 to 100 volume %, preferably 20 to 95 volume %, more preferably 40 to 90 volume %, or much more preferably 70 to 85 volume %. When the athlete's foot medicine or the extracted components of althea are mixed with alcohol, which is very permeant and absorbable into the skin, the athlete's foot medicine or the extracted components of althea penetrate deeply into a hand or a foot.

The invention claimed is:

1. An athlete's foot treatment tool comprising:
   an athlete's foot treatment liquid which is a mixture of athlete's foot medicine and a solvent;
   an inner sock for being worn on a foot and being structured to permeate the athlete's foot treatment liquid and to soak the foot with the athlete's foot treatment liquid;
   an impermeable bag for being worn on the inner sock, being filled with the treatment liquid, and being structured to close around an ankle so as to prevent the medicine from permeating through, evaporating and leaking out;
   a sealing member that seals and closes the impermeable bag around the ankle; and
   an elastic outer sock, the elastic outer sock being a separate element from the impermeable bag, and configured to be worn on the impermeable bag compressing the impermeable bag from outside, after the impermeable bag filled with the athlete's foot treatment liquid has been worn on the inner sock,
   wherein an opening of the inner sock is lower or nearer to a toe than a tightening position of the impermeable bag; and the tightening position or the opening of the impermeable bag is lower and nearer to the toe than an opening of the outer sock.

2. An athlete's foot treatment tool comprising:

an athlete's foot treatment liquid which is a mixture of athlete's foot medicine and a solvent;

an inner glove for being worn on a hand, and being structured to permeate the athlete's foot treatment liquid and to soak the hand with the athlete's foot treatment liquid;

an impermeable bag for being worn on the inner glove, being filled with the treatment liquid, and being structured to close around a wrist so as to prevent the medicine from permeating through, evaporating and leaking out;

a sealing member that seals and closes the impermeable bag around the wrist; and an elastic outer glove, the elastic outer glove being a separate element from the impermeable bag, and configured to be worn on the impermeable bag compressing the impermeable bag from outside, after the impermeable bag filled with the athlete' foot treatment liquid has been worn on the inner glove, wherein an opening of the inner glove is lower or nearer to a fingertip than the tightening position of the impermeable bag; and the tightening position or the opening of the impermeable bag is lower and nearer to the fingertip than an opening of the outer glove.

3. The athlete's foot treatment tool according to claim 1, wherein the athlete's foot medicine is components extracted from althea.

4. The athlete's foot treatment tool according to claim 2, wherein the athlete's foot medicine is components extracted from althea.

5. The athlete's foot treatment tool according to claim 3, wherein:

the athlete's foot treatment liquid includes the solvent and a liquid extract that is formed when the athlete's foot medicine is boiled in the water and decocted, the volume of the water being larger than the athlete's foot medicine; and the athlete's foot treatment liquid is formed when the liquid extract is mixed with the solvent, the volume of the solvent being larger than the liquid extract of the athlete's foot medicine.

6. The athlete's foot treatment tool according to claim 4, wherein:

the athlete's foot treatment liquid includes the solvent and a liquid extract that is formed when the athlete's foot medicine is boiled in the water and decocted, the volume of the water being larger than the athlete's foot medicine; and the athlete's foot treatment liquid is formed when the liquid extract is mixed with the solvent, the volume of the solvent being larger than the liquid extract of the athlete's foot medicine.

7. The athlete's foot treatment tool according to claim 1, wherein the opening of the impermeable bag is closed tightly by the sealing member so as to seal it up, and contained hermetically, wherein even if a patient walks or moves leg, the athlete's foot treatment liquid does not leak out of the bag.

8. The athlete's foot treatment tool according to claim 2, wherein the opening of the impermeable bag is closed tightly by the sealing member so as to seal it up, and contained hermetically, wherein even if a patient moves arm, the athlete's foot treatment liquid does not leak out of the bag.

9. The athlete's foot treatment tool according to claim 7, wherein a space is between the impermeable bag, the inner sock and the foot, and the inner sock has capillarity.

10. The athlete's foot treatment tool according to claim 8, wherein a space is between the impermeable bag, the inner glove and the hand, and the inner glove has capillarity.

11. The athlete's foot treatment tool according to claim 5, wherein the volume of the water is 1 to 12 times larger than the athlete's foot medicine.

12. The athlete's foot treatment tool according to claim 5, wherein the volume of the solvent is 5 to 15 times larger than the liquid extract of the athlete's foot medicine.

13. The athlete's foot treatment tool according to claim 6, wherein the volume of the water is 1 to 12 times larger than the athlete's foot medicine.

14. The athlete's foot treatment tool according to claim 6, wherein the volume of the solvent is 5 to 15 times larger than the liquid extract of the athlete's foot medicine.

15. The athlete's foot treatment tool according to claim 1, wherein the impermeable bag has a square shape.

16. The athlete's foot treatment tool according to claim 2, wherein the impermeable bag has a square shape.

17. A method of treating athlete's foot, the method comprising:

applying the athlete's foot treatment tool of claim 1 to human tissue.

18. A method of treating athlete's foot, the method comprising:

applying the athlete's foot treatment tool of claim 2 to human tissue.

19. The athlete's foot treatment tool according to claim 1, wherein the solvent is alcohol or water.

20. The athlete's foot treatment tool according to claim 2, wherein the solvent is alcohol or water.

* * * * *